(12) United States Patent (10) Patent No.: US 12,611,241 B2

Naraghi (45) Date of Patent: *Apr. 28, 2026

(54) METHODS, SYSTEMS, AND DEVICES FOR THE TREATMENT OF STENOSIS

(71) Applicant: Fred F Naraghi, San Francisco, CA (US)

(72) Inventor: Fred F Naraghi, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/484,439

(22) Filed: Oct. 10, 2023

(65) Prior Publication Data

US 2024/0032976 A1 Feb. 1, 2024

Related U.S. Application Data

(60) Continuation of application No. 16/199,398, filed on Nov. 26, 2018, now Pat. No. 11,779,380, which is a (Continued)

(51) Int. Cl.
| | |
|---|---|
| *A61M 25/10* | (2013.01) |
| *A61B 17/34* | (2006.01) |
| *A61B 17/88* | (2006.01) |
| *A61B 90/00* | (2016.01) |
| *A61B 17/00* | (2006.01) |

(Continued)

(52) U.S. Cl.
CPC ...... *A61B 17/8855* (2013.01); *A61B 17/3415* (2013.01); *A61M 25/1002* (2013.01); *A61B 2017/00557* (2013.01); *A61B 2017/0225* (2013.01); *A61B 2017/0262* (2013.01); *A61B*

2017/564 (2013.01); *A61B 17/7065* (2013.01); *A61B 2090/032* (2016.02); *A61B 2090/037* (2016.02); *A61B 2090/3966* (2016.02); *A61M 2025/105* (2013.01); *A61M 2210/1003* (2013.01)

(58) Field of Classification Search
CPC ............ A61B 17/8855; A61B 17/7097; A61B 2017/00557; A61B 2017/0262; A61F 2/44; A61F 2/4601
See application file for complete search history.

(56) References Cited

U.S. PATENT DOCUMENTS

| | | | | |
|---|---|---|---|---|
| 4,271,839 A | * | 6/1981 | Fogarty ........... | A61M 25/10185 604/920 |
| 5,827,289 A | * | 10/1998 | Reiley ................... | A61F 2/4601 606/86 R |

(Continued)

OTHER PUBLICATIONS

International Preliminary Report on Patentability for PCT/US11/33450 dated Aug. 6, 2012.

*Primary Examiner* — Laura A Bouchelle

(57) ABSTRACT

Catheter system, devices and methods for diagnosing and treating lateral stenosis causing back pain and or leg pain. The devices comprise a tubular part for insertion into a working cannula to self-position itself safely within the foramen, and minimize the risk of displacement medially or laterally, to prevent nerve or dura injury. An expandable membrane is configured to maintain the catheter device within the foramen. Expansion of this membrane would decompress the nerve within the foramen by opening the foraminal canal as the membrane expands.

9 Claims, 17 Drawing Sheets

Related U.S. Application Data continuation-in-part of application No. 15/797,115, filed on Oct. 30, 2017, now Pat. No. 11,045,181, which is a division of application No. 14/492,537, filed on Sep. 22, 2014, now Pat. No. 9,808,233.

(60) Provisional application No. 61/880,372, filed on Sep. 20, 2013.

(51) Int. Cl.
| | |
|---|---|
| *A61B 17/02* | (2006.01) |
| *A61B 17/56* | (2006.01) |
| *A61B 17/70* | (2006.01) |

(56) References Cited

U.S. PATENT DOCUMENTS

| | | | | |
|---|---|---|---|---|
| 6,402,750 | B1 * | 6/2002 | Atkinson | A61B 17/70 606/279 |
| 6,719,773 | B1 * | 4/2004 | Boucher | A61B 17/8855 606/86 R |
| 6,719,795 | B1 | 4/2004 | Cornwall et al. | |
| 6,852,095 | B1 | 2/2005 | Ray | |
| 7,452,351 | B2 * | 11/2008 | Miller | A61B 17/3478 604/509 |
| 7,811,290 | B2 * | 10/2010 | Rabiner | A61B 17/3472 606/94 |
| 7,815,649 | B2 * | 10/2010 | Layne | A61B 17/8858 606/105 |
| 7,955,339 | B2 * | 6/2011 | Schwardt | A61B 17/8855 606/105 |
| 8,114,161 | B2 | 2/2012 | Evans et al. | |
| 8,147,516 | B2 | 4/2012 | Malandain | |
| 8,147,526 | B2 | 4/2012 | Auyoung | |
| 8,152,837 | B2 | 4/2012 | Altarac et al. | |
| 8,167,890 | B2 | 5/2012 | Malandain et al. | |
| 8,167,944 | B2 | 5/2012 | Kim | |
| 8,187,327 | B2 | 5/2012 | Edidin et al. | |
| 8,192,435 | B2 | 6/2012 | Bleich et al. | |
| 8,231,656 | B2 * | 7/2012 | Lee | A61B 17/7068 606/249 |
| 9,757,535 | B2 | 9/2017 | Rajagopalan | |
| 9,808,233 | B2 * | 11/2017 | Naraghi | A61B 17/0218 |
| 11,779,380 | B2 * | 10/2023 | Naraghi | A61B 17/8855 604/506 |
| 2006/0084987 | A1 | 4/2006 | Kim | |
| 2006/0210605 | A1 | 9/2006 | Chang | |
| 2006/0235387 | A1 | 10/2006 | Peterman | |
| 2008/0051894 | A1 | 2/2008 | Malandain | |
| 2008/0208341 | A1 * | 8/2008 | McCormack | A61F 2/4611 623/17.12 |
| 2009/0204150 | A1 | 8/2009 | Hochschuler et al. | |
| 2009/0281626 | A1 | 11/2009 | Farr | |
| 2010/0100133 | A1 | 4/2010 | Carl et al. | |
| 2011/0213301 | A1 | 9/2011 | Auyoung | |
| 2011/0288553 | A1 | 11/2011 | Jansen et al. | |
| 2016/0045192 | A1 | 2/2016 | Naraghi | |

* cited by examiner

Cervical
Vertebrae
C1-C7

Thoracic
Vertebrae
T1-T12

Sacroiliac
Joint

Iliac
Bone

Lumbar
Vertebrae
L1-L5

2

Sacral
Vertebrae
S1-S5

Coccygeal
Vertebrae

Sacrum

Pedicle

Vertebral
Body

Lamina

Spinal
Cord

Lamina

Spinous
Process

Vertebral
Foramen

Vertebral
Body

Pedicle

Lamina

Thecal
Sac

Lamina

Vertebral
Foramen

12

14

Thinning or
compressed
disc

Normal

Degenerated
disc and
osteophytes

Spinal
cord

Bulging
disc

Cervical
vertebrae

Spinal
cord

Cervical
vertebrae

158

102

58

METHODS, SYSTEMS, AND DEVICES FOR THE TREATMENT OF STENOSIS

CROSS-REFERENCE TO RELATED APPLICATIONS

This application is a Continuation of application Ser. No. 16/199,398, filed 26 Nov. 2018 (now U.S. Pat. No. 11,779, 380, issued 10 Oct. 2023), which is a Continuation-in-part of application Ser. No. 15/797,155, filed 30 Oct. 2017 (now U.S. Pat. No. 11,045,181, issued 9 Jun. 2021), which is a divisional of application Ser. No. 14/492,537 filed 22 Sep. 2014 (now U.S. Pat. No. 9,808,233, issued 7 Nov. 2017, which claims the benefit of provisional application Ser. No. 61/880,372, filed 20 Sep. 2013.

FIELD OF THE INVENTION

The present invention relates to devices and apparatus for the treatment of stenosis, and particularly the use of catheter devices in combination with an expandable device for the treatment of stenosis.

BACKGROUND OF THE INVENTION

Disc herniation and degenerative disorders of the lumbar spine are prevalent, deteriorate the quality of life, and are a major health care concern of the general population.

Lumbar spinal stenosis is defined as the narrowing of the spinal canal in the lumbar region. This is as a consequence of several pathologic conditions, the most common of which is chronic degenerative spondylosis. Other common causes of stenosis include disc herniation, facet hypertrophy, or congenital causes. Absolute stenosis has been defined as a decrease in the midsagittal lumbar canal diameter of less than 10 mm on MRI.

Although there are different ways of describing stenosis, generally the stenosis of the spinal canal can occur centrally or laterally. Patients often present with a combination of symptoms from both central and lateral stenosis.

Lateral stenosis can be further classified into three distinct zones: the lateral recess, foraminal zone, and extraforaminal zone.

Lateral recess stenosis is caused by overgrowth of the superior articular facet, and ligamentum or capsular redundancy or hypertrophy. Foraminal stenosis may be due to a foraminal disk protrusion, posterior osteophyte formation, ligamentum or capsular hypertrophy, or loss of vertical height from degenerative collapse of the disk. The extraforaminal zone, which is defined as the area lateral to the intervertebral foramen, is most often affected by far-lateral disk and osteophyte pathology.

Spinal nerves (also referred to as "nerve roots") originate from the spinal cord, remain within the central portion of the spinal canal, and then exit through the foramen or neuroforamen. The neuroforamen primarily contains the nerve root exiting from each corresponding intervertebral level. It also contains the dorsal root ganglion (DRG), a structure that contains the cell bodies of the afferent sensory neurons. DRG has a variety of sensory receptors that are activated by mechanical, thermal, chemical, and noxious stimuli. If DRG is impinged within the foramen, in lateral stenosis cases, it can be quite painful, and it can become a major source of pain generation.

Spinal stenosis is treated conservatively initially with therapy modalities and medications. Epidural injections with local anesthetics and steroids may be used next. However, these injections may relieve pain for a limited period of time only. More importantly, injections typically do not influence or improve the functional outcome of patient condition. The majority of patients report little substantial improvement in symptoms with repeated treatment.

Decompression surgery is considered only after conservative treatments have failed. Currently, there are 2 surgical approaches to decompress the lateral portion of the canal: medial (or "inside-out"), and lateral (or "outside-in", or "transforaminal"). Each has its advantages and disadvantages. The advantage of the medial approach includes surgeon familiarity through a laminotomy. The disadvantage of medial approach is significant bone resection required to get to the foramen, which is located more laterally, and possible dural tear. This excess bone resection may lead to an iatrogenic instability of the spinal segment if it is extensive. Also, trying to reach under the facet to decompress the foraminal zone can result in possible injury to the nerve root injury due to the deep and lateral position of the nerve root within the foramen. The advantage of transforaminal approach includes less or no bone resection, less risk of dural tear, faster recovery due to less muscle dissection, less risk of possible epidural scar formation. The disadvantages of transforaminal approach include technically demanding approach, and difficulty in visualizing the content of foramen from the lateral side.

Balloon dilation is currently used in various parts of the body including esophagus, urethra, coronary arteries, and peripheral arteries. Additionally, balloons have been used to create a void within vertebral body to restore the height of fractured vertebrae and allow for filling of the void with cement or bone graft to stabilize a vertebral fracture, commonly referred to as Kyphoplasty.

Balloons have also been used to aid in separating tissues or vital structures away from a targeted area to be addressed surgically in various parts of the body, including abdominal surgery.

While there have been improvements in the treatment of stenosis, there is further room for improvement, particularly with respect to providing the correct amount of pressure to a particular area spinal cord.

SUMMARY OF THE INVENTION

The present invention is directed towards the use of systems and devices that employ catheter devices in combination with expandable structures, e.g. balloons, to treat stenosis. The balloons are utilized to perform foraminal decompression, which allows for non-surgical or less invasive surgical treatment of lateral spinal stenosis by modifying the underlying pathophysiology. The systems and devices of the present invention includes inflatable members, e.g. balloons, that are designed to provide varying levels of volume to treat lateral spinal stenosis. The balloons of the present inventions also provide a volumetric range for treatment of the spinal stenosis.

The systems and devices of the present invention also includes catheters for delivering the balloons of varying lengths, thereby more accurately treating a particular area within the spinal cord.

The methods of the present invention include using the systems and methods used for treating stenosis. The methods can be used for treating spinal stenosis.

The systems and methods of the present invention also use expandable members that are designed to reach a certain volume and deflate, thereby minimizing trauma to the spinal are.

The systems and methods of the present invention also may treat the cervical area of the spine, as well as to be use for neck and arm pain associated with spinal issues.

DETAILED DESCRIPTION OF THE INVENTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention. While the present invention pertains to systems, devices, and surgical techniques applicable at virtually all spinal levels, the invention is well suited for achieving dynamic stabilization of transverse processes of adjacent lumbar vertebrae. It should be appreciated, however, the systems, device, and methods so described are not limited in their application to the spine, and could be employed for use in treating different types of stenosis throughout the body.

Figure 1:
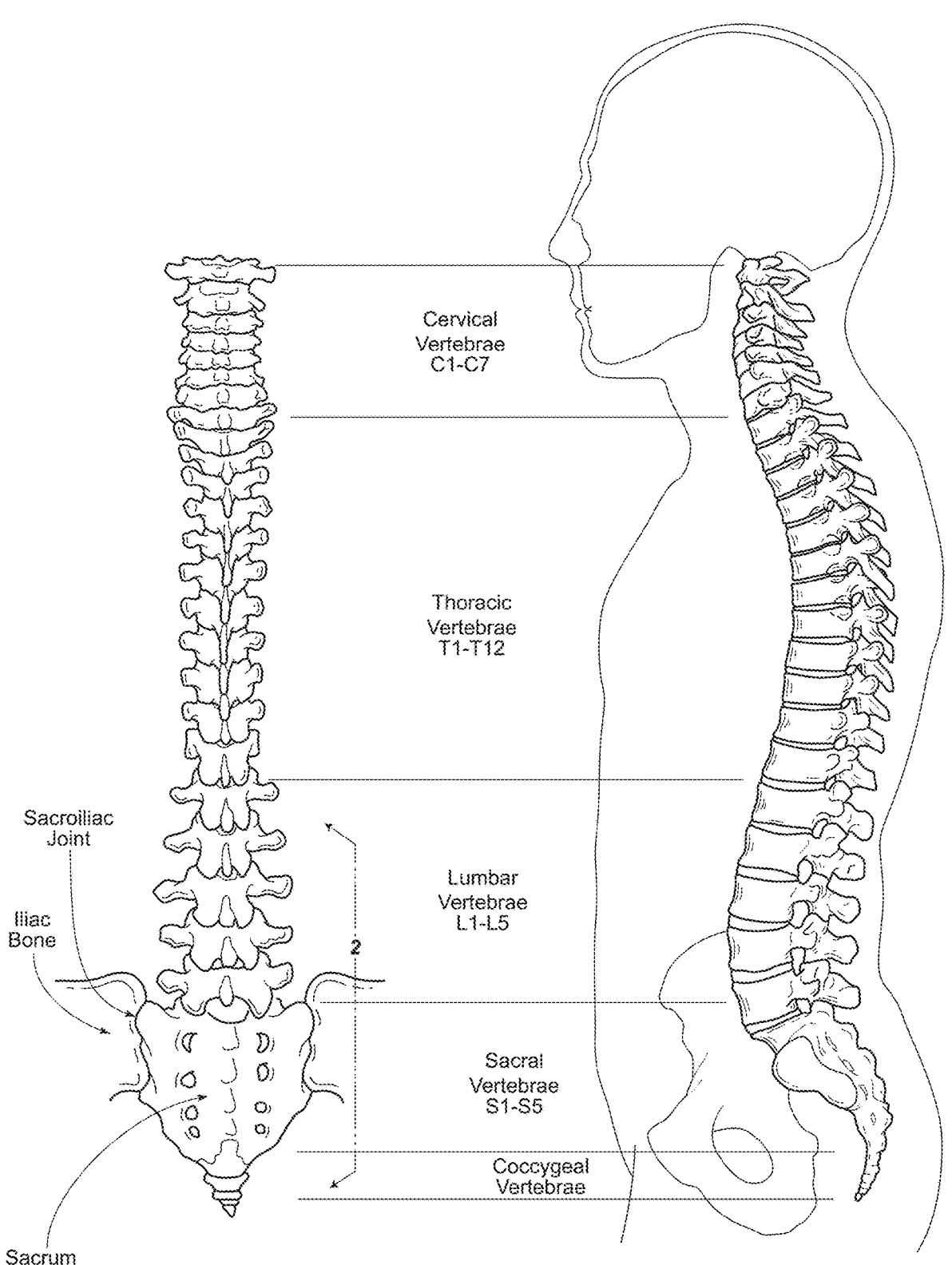
FIG. 1 is an anatomic view of a human spine, showing the different regions of vertebrae.

The spine (see FIG. 1) is a complex interconnecting network of nerves, joints, muscles, tendons and ligaments. The spine is made up of small bones, called vertebrae, which are named according to the region of the body they occupy. The vertebrae in the head and neck region are called the cervical vertebrae (designated C1 to C7). The vertebrae in the neck and upper back region are called the thoracic vertebrae (designated T1 to T12). The vertebrae in the lower back region are called the lumbar vertebrae (numbered L1 to L5). The vertebrae in the pelvic region are called the sacral vertebrae (numbered S1 to S5).

Figure 2:
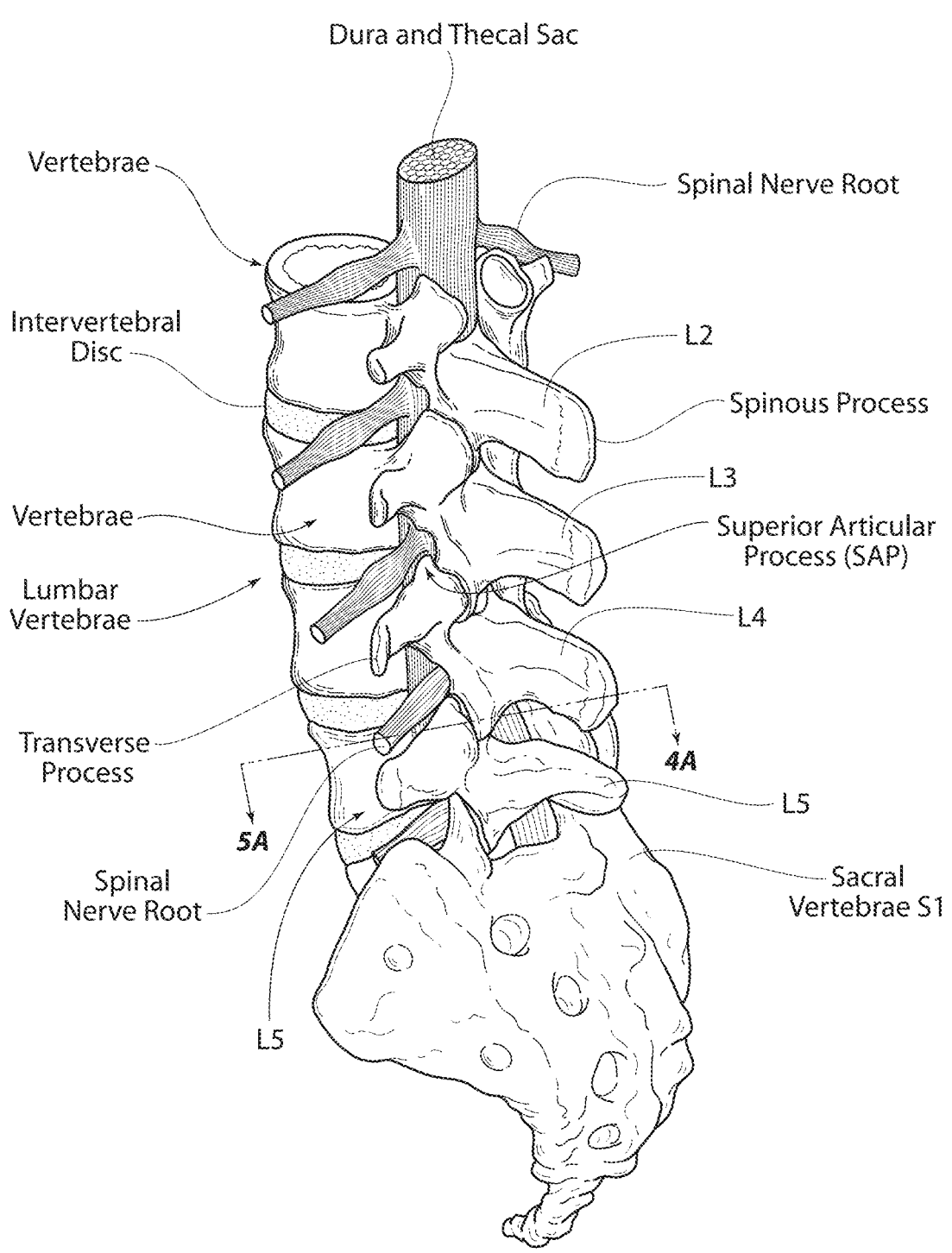
FIG. 2 is an anatomic ipsilateral view of the lower back region of the spine, showing the lumbar vertebrae L2 to L5, the sacral vertebrae S1 to S5, and the coccygeal vertebrae.
Figure 3:
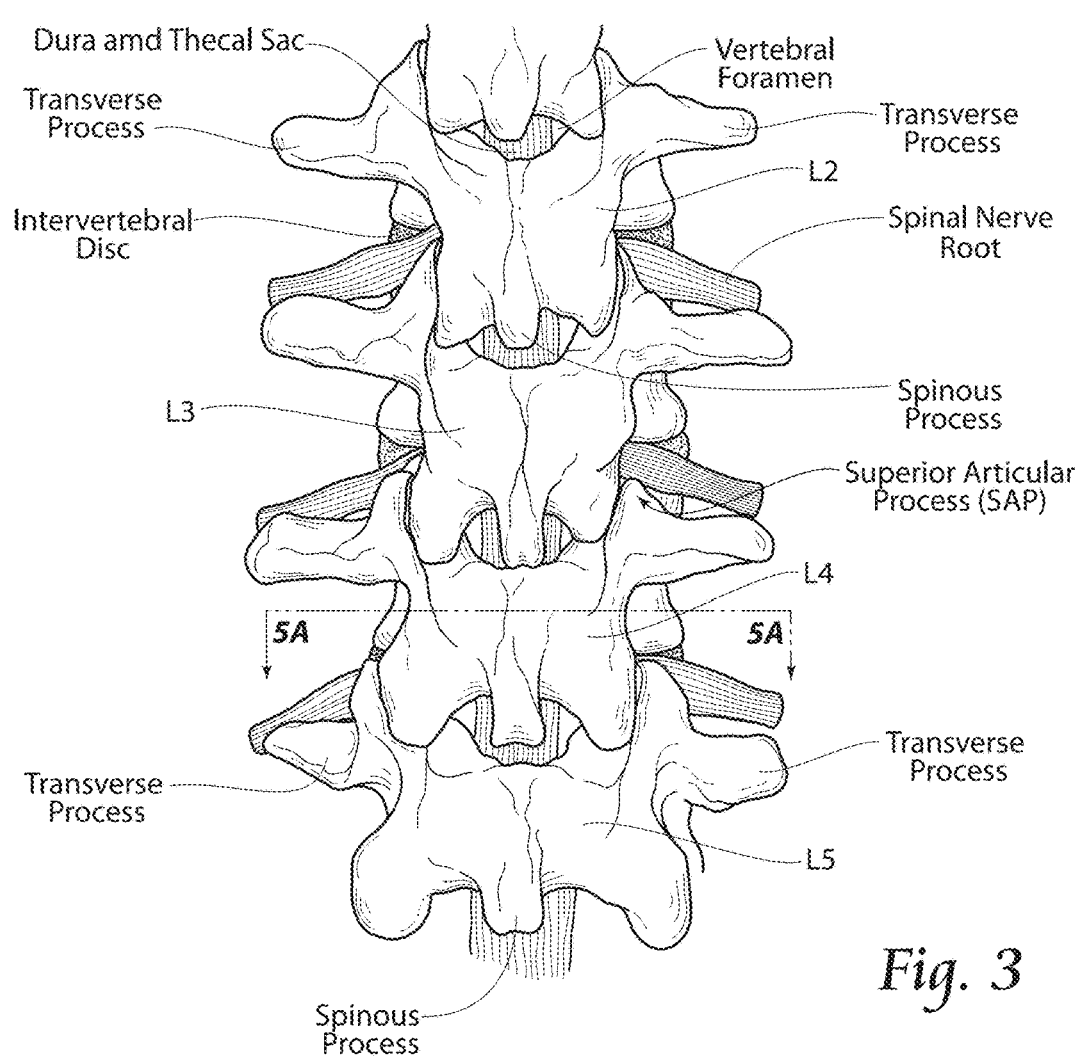
FIG. 3 is an anatomic posterior view of the lower back region of the spine, showing the lumbar vertebrae L2 to L5.
Figure 4:
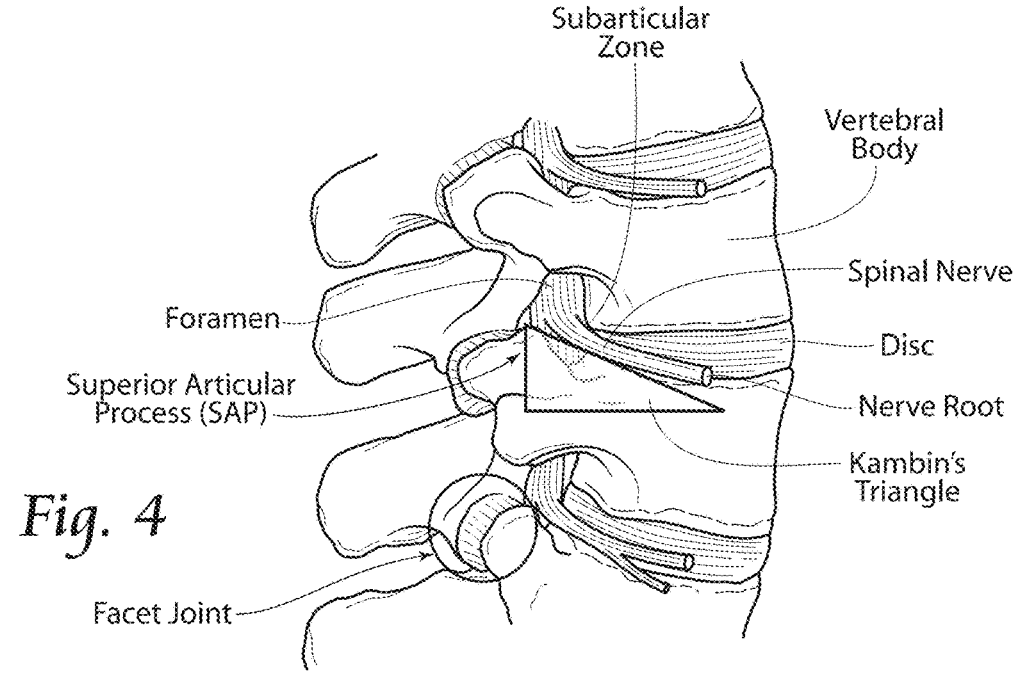
FIG. 4 is an anatomic distal view of the view of the spine shown in FIG. 3.

The vertebrae protect and support the spinal cord. They also bear the majority of the weight put upon the spine. As can be seen in FIG. 4A, vertebrae, like all bones, have an outer shell called cortical bone (the vertebral body) that is hard and strong. The inside is made of a soft, spongy type of bone, called cancellous bone. The bony plates or processes of the vertebrae that extend rearward and laterally from the vertebral body provide a bony protection for the spinal cord and emerging nerves. The vertebrae also protect the thecal sac as shown in FIGS. 2 and 3. The thecal sac contains the nerve roots for the spinal cord. The spinal cord ends around L1-L2 vertebrae, with the thecal sac continuing downwardly from there.

The configuration of the vertebrae differ somewhat, but each (like vertebrae in general) includes a vertebral body (see FIG. 5A), which is the anterior, massive part of bone that gives strength to the vertebral column and supports body weight. The vertebral canal is posterior to the vertebral body and is formed by the right and left pedicles and lamina. The pedicles are short, stout processes that join the vertebral arch to the vertebral body. The pedicles project posteriorly to meet two broad flat plates of bone, called the lamina. The arrangement can also be viewed in FIG. 4.

Other processes arise from the vertebral arch. For example, two superior articular processes ("SAP") project upward from vertebral arch and provide an area for adjacent vertebrae to fit together with one another. Three other processes—the spinous process and two transverse processes—project from the vertebral arch and afford attachments for back muscles, forming levers that help the muscles move the vertebrae.

FIG. 2 shows the S1 sacral vertebra and the adjacent fourth and fifth lumbar vertebrae L4 and L5, respectively, in a lateral view (while in anatomic association). The sacral and lumbar vertebrae are in the lower back, also called the "small of the back." FIG. 3 shows the fourth and fifth lumbar vertebrae L4 and L5 from a different, more posterior, perspective.

Figure 5A:
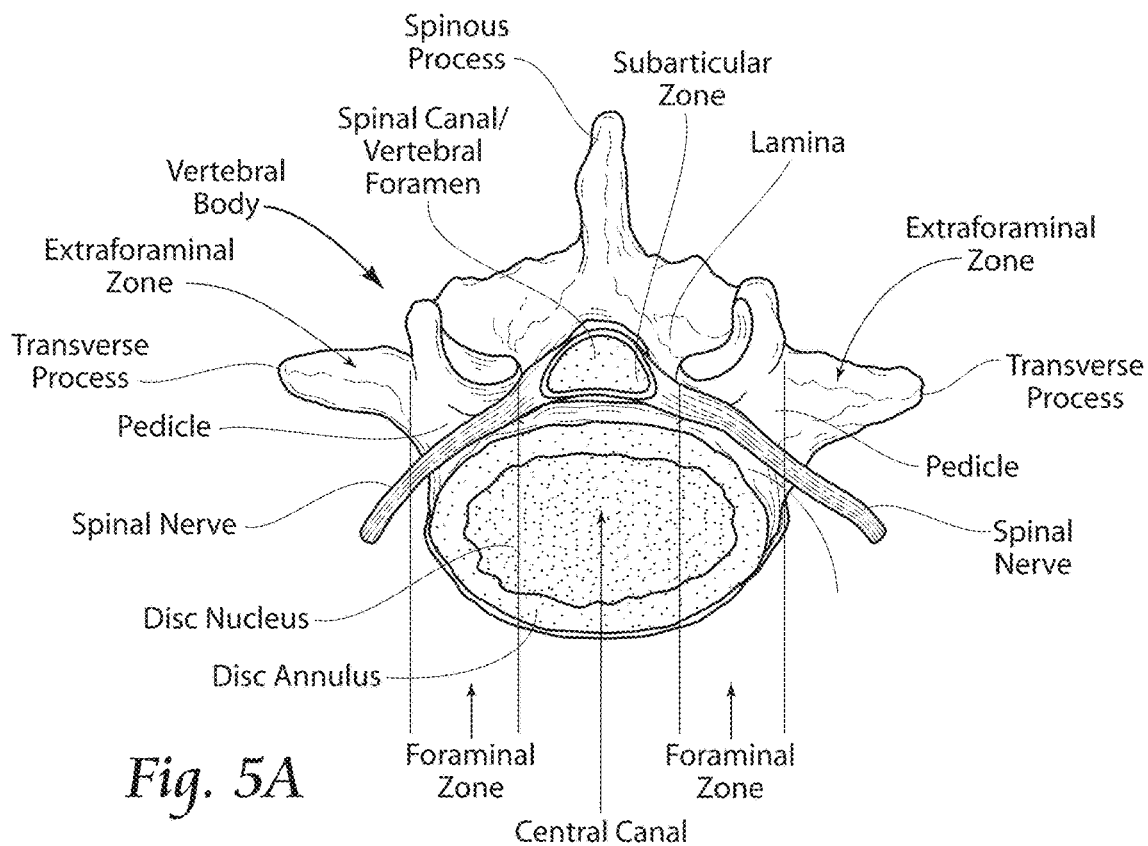
FIG. 5A is an anatomic superior view of a vertebral body, taken along line 5A—5A of FIG. 3, depicting the central canal, foraminal zone, and the extraforaminal zone of the vertebral body.

As previously described, between each vertebra is a soft, gel-like "cushion," called an intervertebral disc (see FIG. 2). These flat, round cushions act like shock absorbers by helping absorb pressure and keep the bones from rubbing against each other. The intervertebral disc also binds adjacent vertebrae together. The intervertebral discs can bend and rotate a bit but do not slide. Along with the invertebral discs, the vertebrae also provide protection for the spinal cord and thecal sac by forming the vertebral foramen (FIG. 5A). The foramen may be depicted with three zones, the foraminal zone, the central canal, and the extraforaminal zone. Stenosis may occur in any of these zones of the foramen, and it is intended that the methods and systems of the present invention would address stenosis in any of these areas.

Figure 5B:
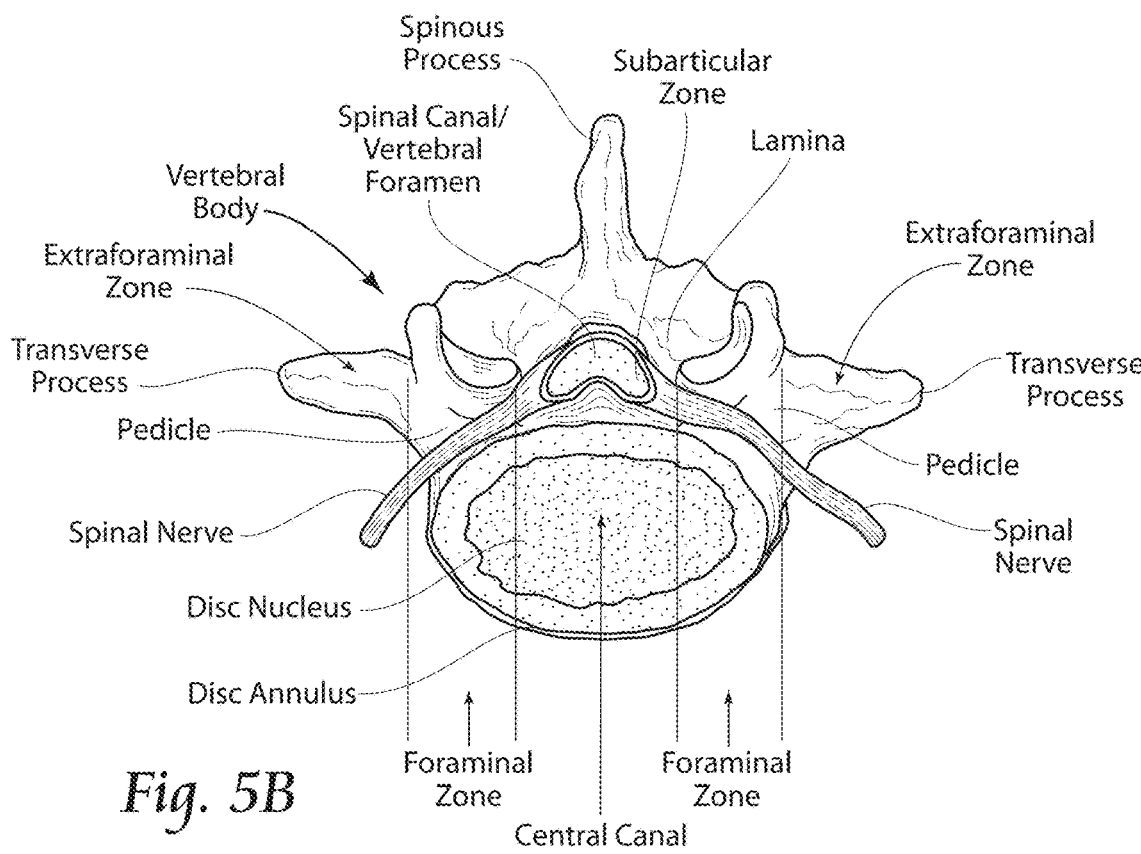
FIG. 5B is an anatomic superior view of a vertebral body, taken along line 5A—5A of FIG. 3, but showing spinal stenosis affecting the region.

FIG. 5A shows a vertebra with a normal vertebral foramen. The vertebral foramen provides an open spinal canal for the spinal cord and the thecal sac to reside. FIG. 5B shows a vertebra with abnormal narrowing of the vertebral foramen, e.g. showing spinal stenosis. As previously explained, when spinal stenosis occurs, the spinous process overgrows into the vertebral foramen, thereby impinging on the spinal cord and/or the thecal sac and the related spinal nerves. The impingement into the vertebral foramen causes nerve root compression and spinal stenosis, with resulting pain, and discomfort.

As previously discussed, each vertebra also has two other sets of joints (see FIGS. 2 and 3). For a given vertebra (e.g., L4), one pair of facet joints faces upward (called the superior articular process, SAP) and the other pair of facet joints faces downward (called the inferior articular process, IAP). The inferior and superior processes mate, allowing motion (articulation), and link vertebrae together. Facet joints are positioned at each level to provide the needed limits to motion, especially to rotation and to prevent forward slipping (spondylolisthesis) of that vertebra over the one below.

Figures 6A, 6B, 7A, 7B, 8:
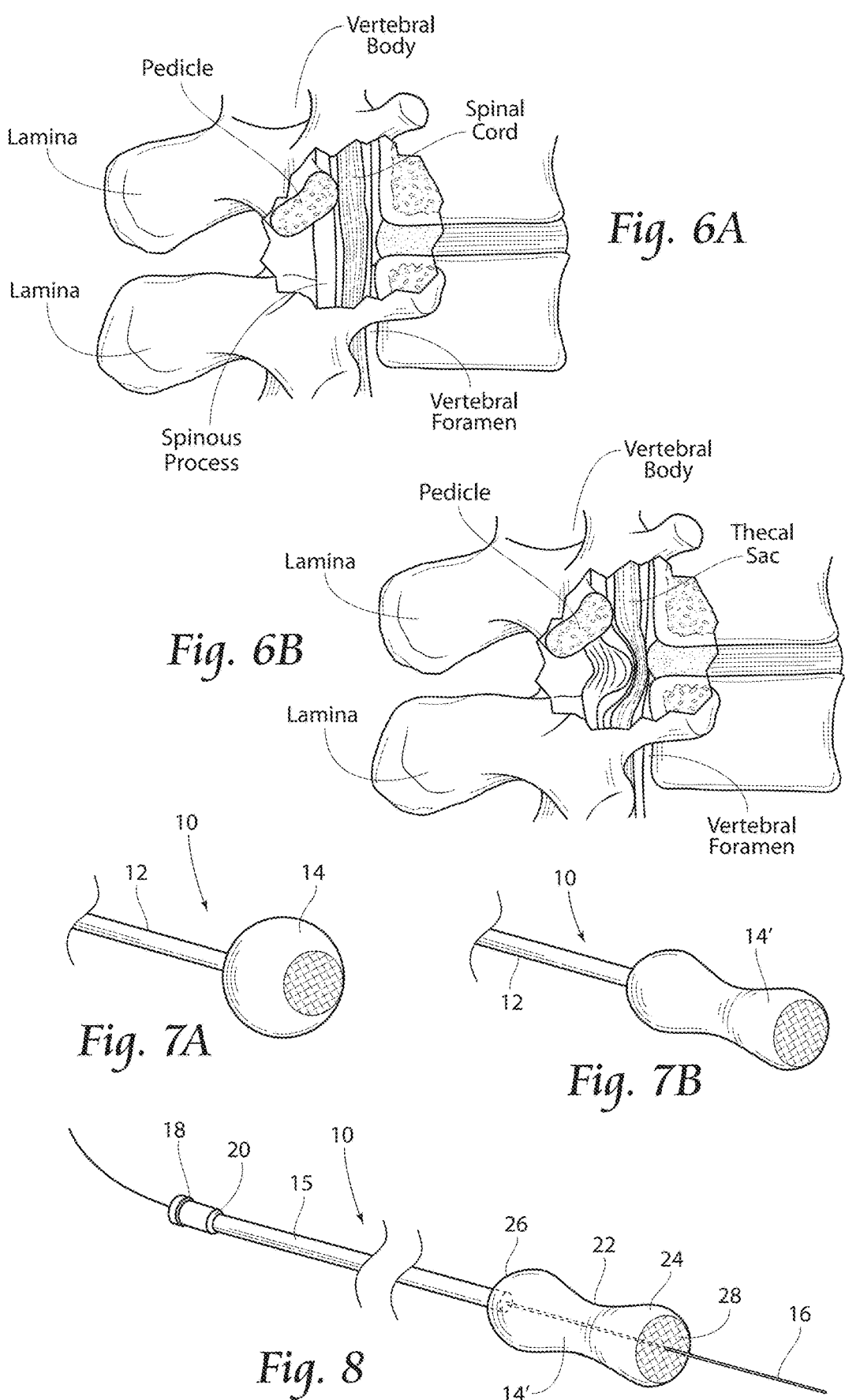
FIG. 6A is a partially cut-away view of the spinal region as shown in FIG. 3.
FIG. 6B is a partially cut-away view of the spinal region as shown in FIG. 3, but showing spinal stenosis in the region.
FIG. 7A is a partial view of a delivery device 10 of the present invention being used in the present invention, with a generally spherical inflatable member being used within the delivery device.
FIG. 7B is a partial view of a delivery device as shown in FIG. 7A, with the exception that the inflatable member has a generally barbell shape.
FIG. 8 is partial cut-away perspective view of a delivery device of the present invention, with the inflatable member being inflated and a guide wire within the inflatable member.

FIGS. 6A and 6B provide another perspective to demonstrate the anatomy shown and described in FIGS. 5A and 5B. The partially cut-away view in FIG. 6A shows the thecal sac sitting within the vertebral foramen, being protected by the vertebral body, as described above. However, as shown in FIG. 6B, an impingement of the thecal sac is shown. The disc is pushing into the thecal sac, while the vertebral facet pushes forward into the thecal sac. Such an impingement is often a condition of facet hypertrophy, or an enlargement or degenerative change in the facet joint. These degenerative changes in the spinous process and the spine in general can adversely affect the ability of each spinal segment to bear weight, accommodate movement, and provide support. When one segment deteriorates to the point of instability, it can lead to localized pain and difficulties.

Facet joint fixation procedures have been used for the treatment of pain and the effects of degenerative changes in the lower back. In one conventional procedure for achieving facet joint fixation, the surgeon works on the spine from the back (posterior). The surgeon passes screws from the spinous process through the lamina and across the mid-point of one or more facet joints.

II. Representative System of a Delivery Device Used in Treating Stenosis

The present invention is directed towards a system for treating and addressing conditions caused by stenosis of the joints and is particularly useful for treatment of spinal stenosis. The system will provide relief of the vertebral column and the discs from impinging on the spinal cord and/or thecal sac located in the vertebral foramen.

As shown in FIG. 8, the system 10 generally comprises a catheter 12 that houses an expandable member 14, 14', e.g. a balloon. As will be discussed in further detail, the catheter will generally be introduced into the vertebral foramen by way of a working cannula 15. The system may also include a guide wire 16 to assist in directing the catheter into the vertebral foramen. Preferably the guide wire 16 is attached to the working cannula 14 at the proximal end 18 by a screw fitting 20 or other common arrangement that will allow the guide wire to be attached or removed as necessary.

FIGS. 7A and 7B demonstrate different shaped expandable members 14, 14' that may be used in the system. In FIG. 7A, a spherical expandable member 14 is shown, while a dumbbell-shaped expandable member 14' is shown in FIG. 7B. The dumbbell-shaped expandable member 14' may be designed so that the middle section 22 is less expandable than the distal 24 and proximal portions 26 (see FIG. 8). In certain situations, as discussed below, such an arrangement will provide for the expandable member 14' to act as anchor between the medial and lateral sides of a vertebral facet joint. The expandable member 14' may be made of differing materials that allow the distal 24 and proximal portions 26 to expand quicker than the central portion 22 of the expandable member 14'.

Figure 9:
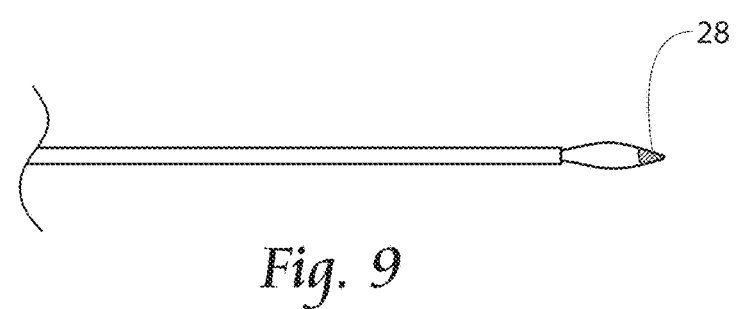
FIG. 9 is a partially cut-away view of the delivery system of the present invention, demonstrating a radiopaque marker on the inflatable member.

To assist in proper positioning of the expandable member 14, 14', a marker 28 may be located on the end or tip of the expandable member. For example, a radiopaque marker (demonstrated in FIG. 9) may be used to visualize the expandable member 14, 14' position during fluoroscopy. Alternatively, an echogenic marker (demonstrated in FIG. 10) could be used in combination with an ultrasound device for ultrasonic guidance of the expandable member 14, 14'.

To assist in the treatment of stenosis, the catheter 12 is also designed so that the volume within the expandable member 14, 14' can be measured, so that proper positioning of the expandable member 14, 14' when deployed will occur. The volume may also be measure, for example with the use of a dyed fluid being injected into the expandable member.

The system is also designed so that various solutions, treatments, and substances can be injected into the treated area. For example, anesthetics, steroids, growth factors, stem cell material, or other medicinal materials, may be injected through the system into the treated foraminal space.

As will be discussed below, the system 10 is designed so that the expandable members can be advance into the vertebral foramen to address the stenosis and, eventually, removed from the foramen once the stenosis has been addressed.

III. Representative Methods for the Treatment of Stenosis

The present invention includes methods for the treatment of stenosis. As generally discussed above, stenosis is caused by an impingement into a foramen, thereby constricting the thecal sac, nerves, or spinal cord that may be located within the foramen. The methods generally are directed towards the use of expandable members 14, 14' such as balloons that are inserted into the foramen. The expandable members are inflated in a step-like process to treat the impingement.

As demonstrated below, the methods of the present invention can be used for the treatment of spinal stenosis. Spinal stenosis may be caused by the overgrowth of the superior articular facet, ligamentum, capsular redundancy, hypertrophy, or a combination of these. As described below, there are two main ways of addressing the spinal stenosis according to the present invention: 1) a mid-line approach that would generally be performed during a laminotomy, or 2) a percutaneous approach.

Furthermore, the methods described below address issues and problems of the prior art, namely having adequate control of the inflatable members 14, 14' used in the methods. The described methods are capable of being directed to specifically localize and target a specific point within the neuroforamen. As will be discussed, the present invention allows for control of the inflation of the discussed inflatable members 14, 14', including control of variables such a pressure and volume for the inflatable members, which allows for precise treatment of the stenosis.

Figure 11:
FIG. 11 depicts a patient lying on an operating table, with the patient's back exposed, which demonstrates an initial step in performing a procedure according to the present invention.
Figure 12:
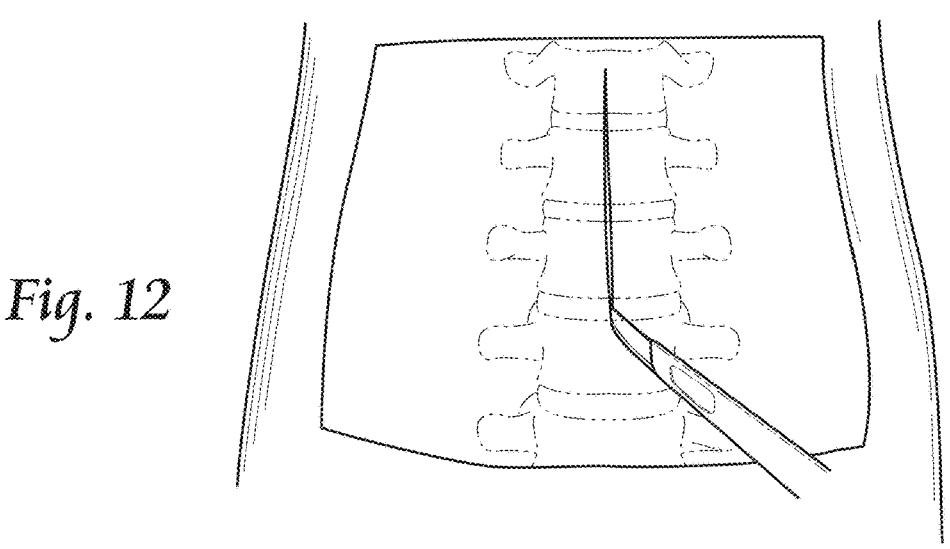
FIG. 12 depicts an incision in the area depicted in FIG. 11.
Figure 13:
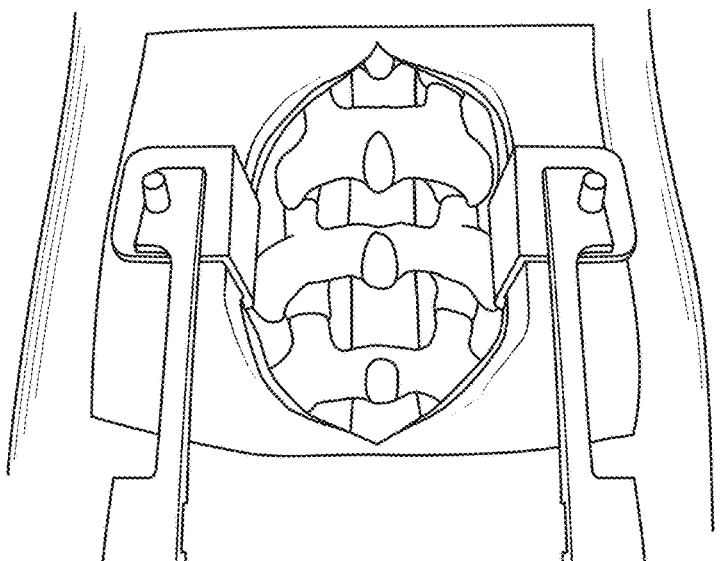
FIG. 13 depicts the area around the incision being resected to allow access to the area of the spine where insertion of a delivery system according to the present invention will take place.

As shown in FIG. 11, a patient will be positioned to provide access to the patient's back, such as for a laminotomy. A cut will be made along the length of the spine (FIG. 12), and the area will be resected to provide access to the spinal area (FIG. 13). The expandable member will then be inserted into the resected area, posteriorly to anteriorly until a desired placement and position is found so that the expandable member 14 can be properly inflated.

Figure 14:
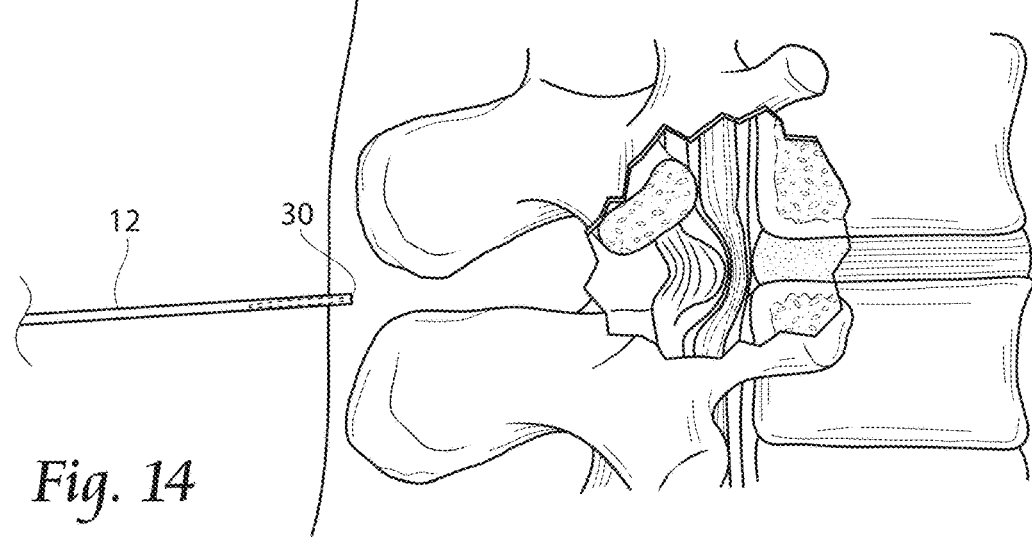
FIG. 14 is a partially cut-away view of the spinal region as shown in FIG. 6A showing the first position of the delivery system near the spinal region.
Figure 15:
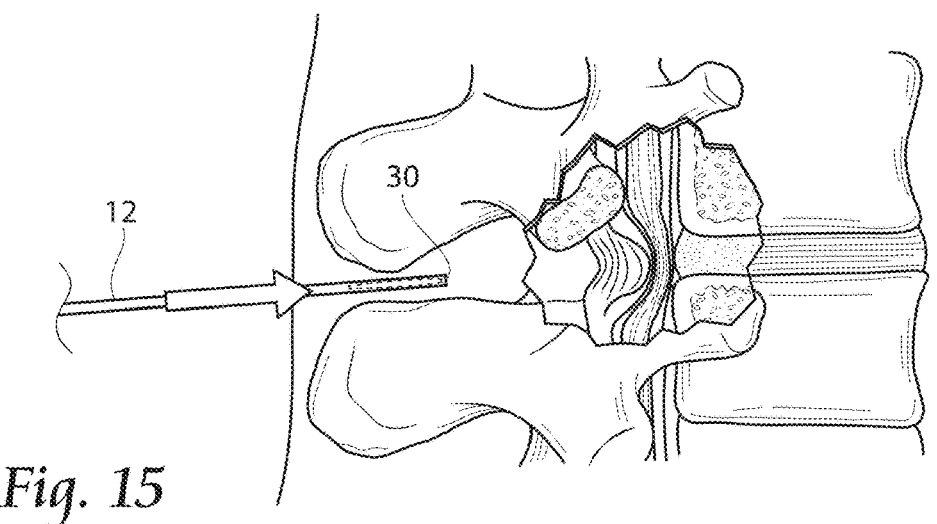
FIG. 15 depicts a further step in advancing the delivery system into the spinal area.
Figure 16:
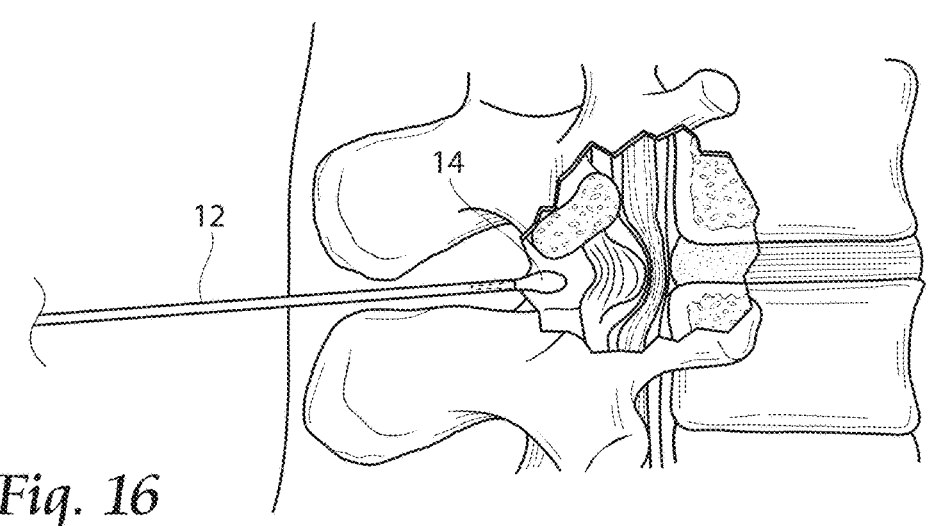
FIG. 16 depicts another further step in advancing the delivery system in to the spinal area to be treated, with the inflatable member being slightly expanded.

FIG. 14 shows an initial positioning of the catheter 12 as it is introduced posteriorly through the laminotomy site. The tip 30 of the catheter 12 is positioned at the beginning of the subarticular zone. The catheter 12 will be slowly moved forwardly in a posterior to anterior direction, further into the foramen (FIG. 15), wherein the expandable member 14 is slowly inflated (FIG. 16). As previously discussed, the positioning of the expandable member 14 will be monitored by the use of a marker, such as a fluoroscopic or echogenic marker.

Figure 17:
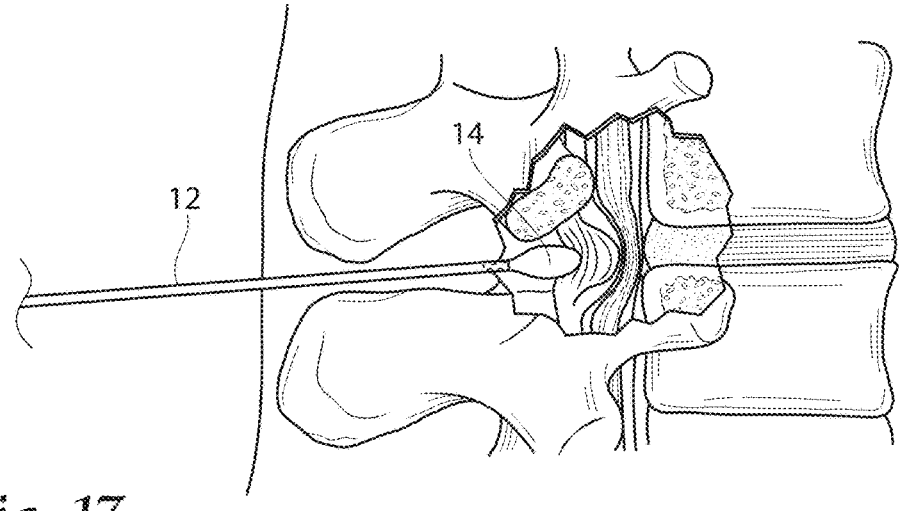
FIG. 17 depicts another further step in advancing the delivery system into the spinal area to be treated.
Figure 18:
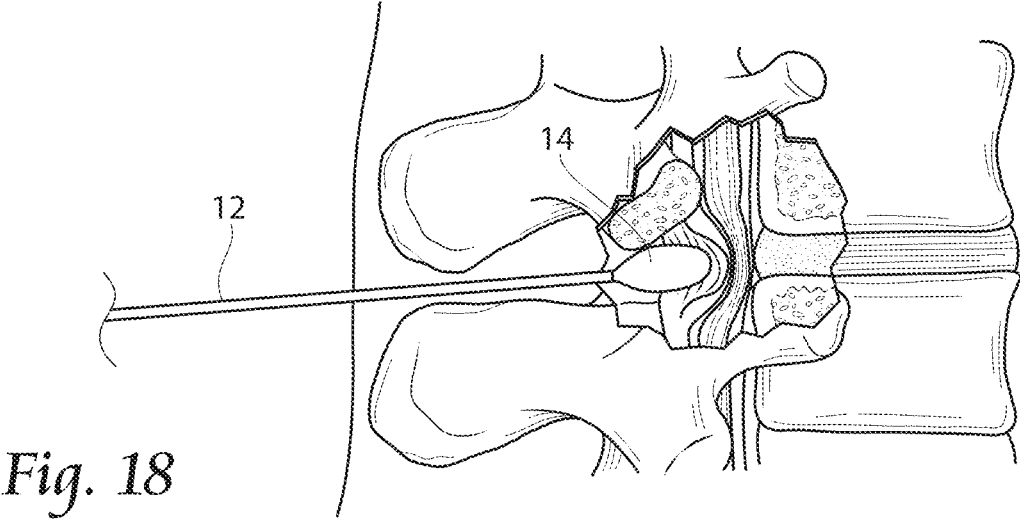
FIG. 18 depicts the delivery system being positioned as desired within the spinal area.

Once the catheter 12 and the expandable member 14 are determined to be in a safe position, the catheter 12 may be further inserted into the foramen, with the expandable member being further inflated (FIGS. 17 and 18). The process of insertion and inflation will be repeated until the surgeon has determined that the expandable member is properly positioned. Further, if it is determined that the expandable 14 member may not be properly inflated or positioned after any particular step, the catheter 12 can be retracted and/or the expandable member 14 can be partially deflated to reposition the catheter 12 and the expandable member 14. In this manner, the stepped process will do minimal agitation or discomfort to the patient while carrying out the process.

Figure 19:
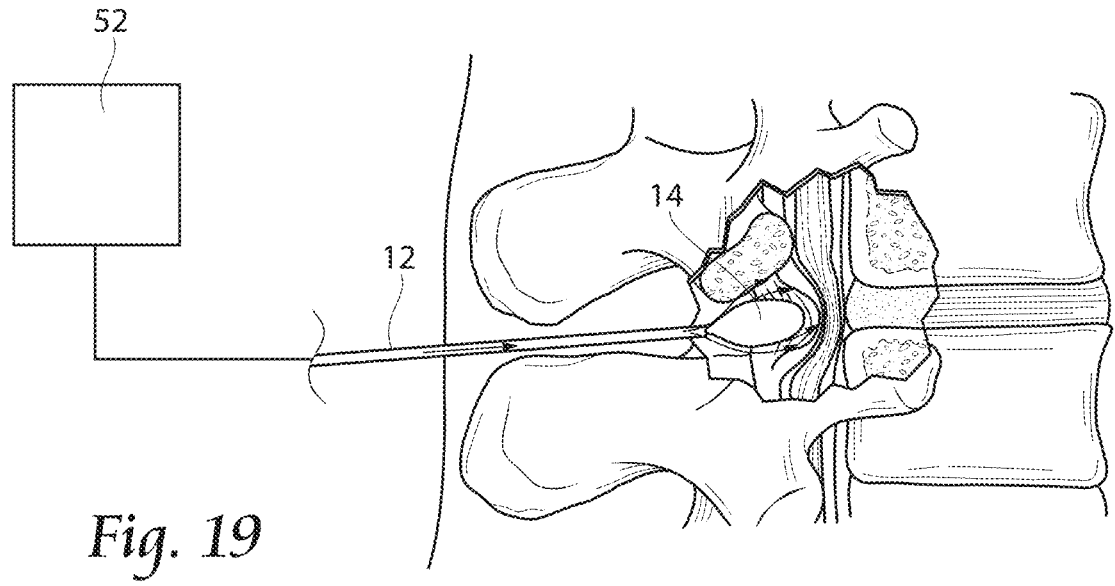
FIG. 19 depicts the delivery of a medicament or other solution to the treated area.
Figure 21:
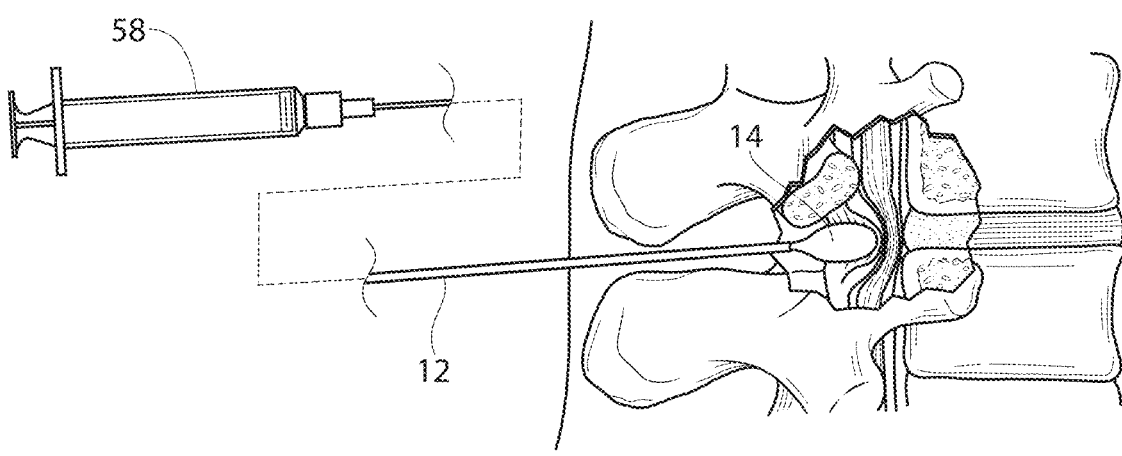
FIG. 21 depicts an inflatable member being inflated.

If necessary, a medicinal or therapeutic material such as anesthetics, steroids, growth factors, stem cell material, or other materials, may be injected through the system into the treated foraminal space, as demonstrated in FIG. 19. As shown, the materials are injected using the same catheter 12 as that which delivered the expandable member 14. However, it may be possible that a second catheter dedicated to the delivery of these materials may also be employed. FIG. 19 includes a delivery device 52, which can includes such delivery devices as a syringe 158 (see FIG. 21).

Figure 20:
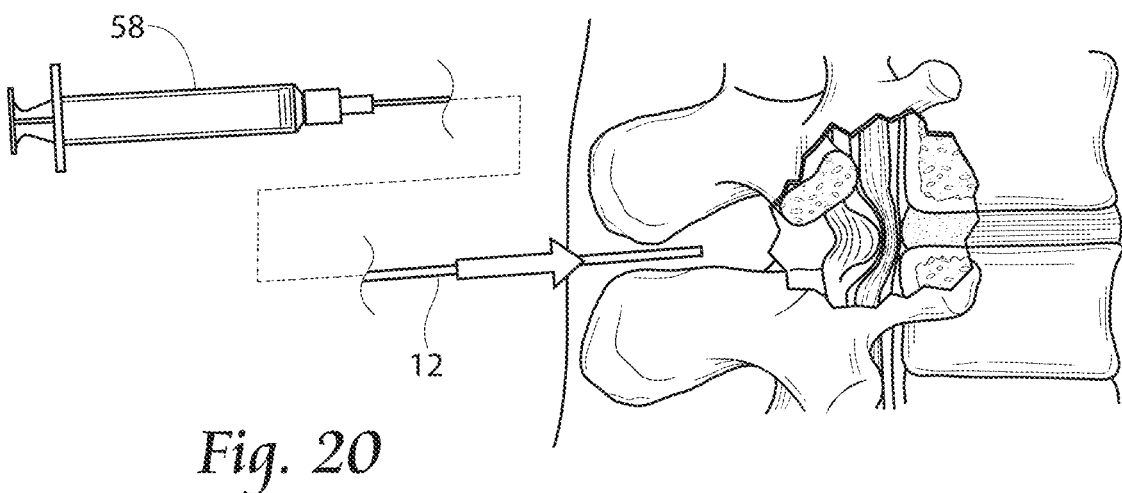
FIG. 20 depicts a delivery system according to the present invention, with an instrument capable of adjusting the volume of an inflatable member.

As is appreciated from the above discussion, one of the advantages of the present invention is the minimization of pain or trauma during the treatment process. FIGS. 20-23 describe a further advantage of the present invention that will assist in minimizing such issues. Furthermore, as depicted, the processes and inventions minimize trauma, while providing a more efficient FIG. 20 depicts a syringe 58, which can be coupled to the cannula 12 for eventual delivery of the inflatable members 14. The syringe 58 allows for contrast to be delivered to increase the volume within the inflatable member 14, as previously discussed, and as demonstrated in FIG. 21. As will be appreciated with respect to FIGS. 22 and 23, the design of the inflatable members 14 allows the user to inflate the inflatable members 14 with a syringe, without having to monitor the pressure being delivered.

Figure 22:
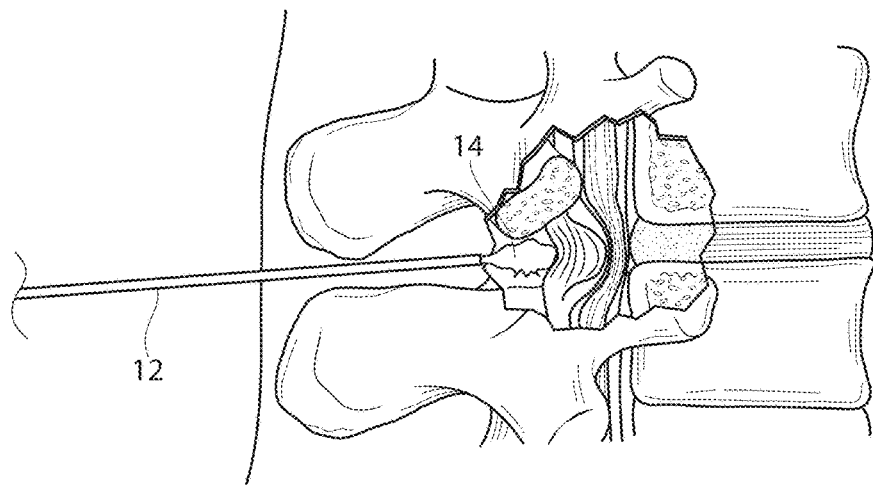
FIG. 22 depicts an inflatable member being overinflated, with the inflatable member being deflated for removal from the spinal area.

FIG. 22 demonstrates another advantage of the present invention. When delivering the inflatable member 14, it may be unintentionally overinflated. Prior art inflatable members would not resist such overinflation, and could cause stress or trauma if expansion in the spinal area happened too quickly. The inflatable members 14 of the present invention, may include a surface area 17, wherein the surface area 17 is less thick than the rest of the inflatable member 14 (see FIG. 23). This allows for the inflatable member 14 to deflate if overinflated, as shown in FIG. 22. While the inflatable member 14 could be designed of a material having one thickness that will also deflate or burst if overinflated, the incorporation of the surface area 17 allows for a more controlled deflation (FIG. 22), thereby minimizing the chance any ruptured pieces of the inflatable member 14 remaining in the spinal area, if overinflation does incur.

Figure 23:
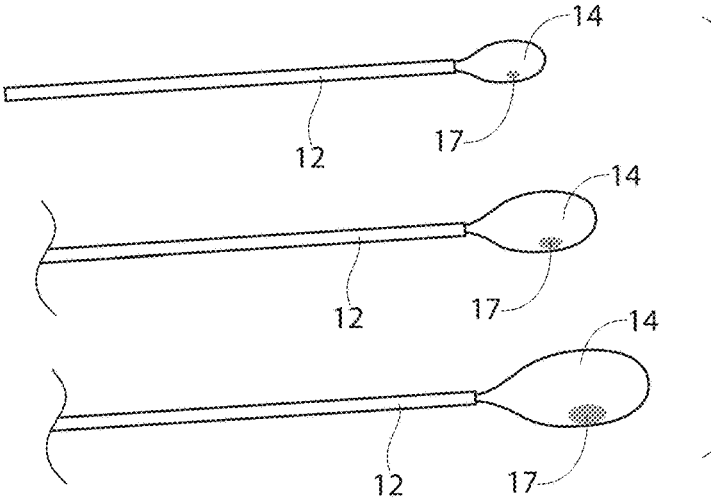
FIG. 23 depicts inflatable members of varying sizes, depicting a thinner area than the entire inflatable member.

Further, the present invention also utilizes inflatable members 14 having varying sizes, shown in FIG. 23, which will assist in the step process for treating stenosis. For example, the inflatable members can range from 0.2 mL to 10 mL, to deliver various levels of expansions and provide for a steady and incremental expansion process. Because the inflatable members 14 are designed only to expand to a particular size prior to larger inflatable members used in the treatment, the expansion is easily carried out with the use of the syringe 58.

The present invention also takes into account proper treatment of stenosis is dependent on the particular area of

Figure 24:
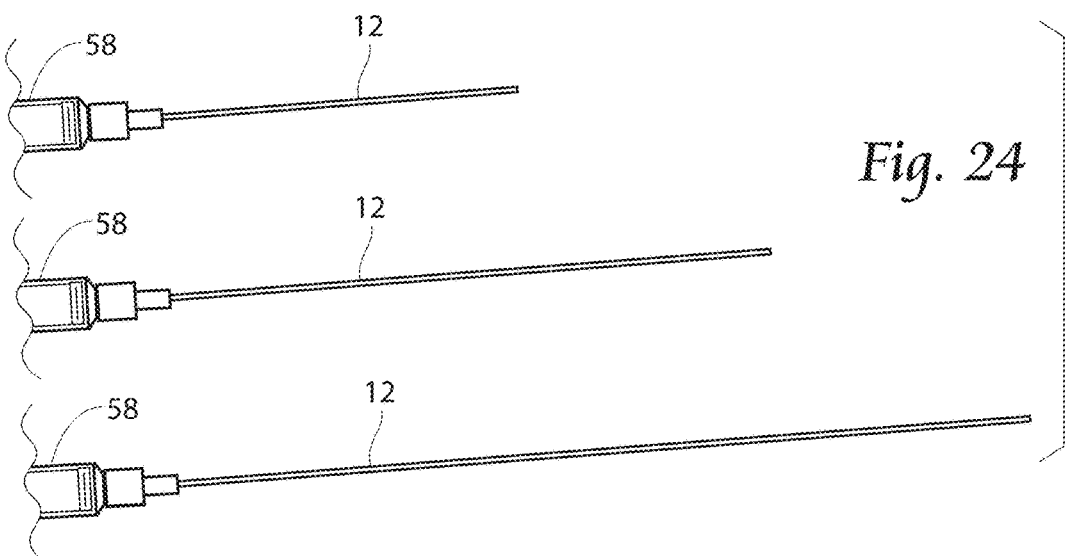
FIG. 24 provides catheters of varying lengths used in the present invention.

9 the spine, as well as the height of the patient being treated. As such, FIG. 24 shows cannulas 12 of varying lengths, e.g. between 10 cm and 40 cm.

Figure 25:
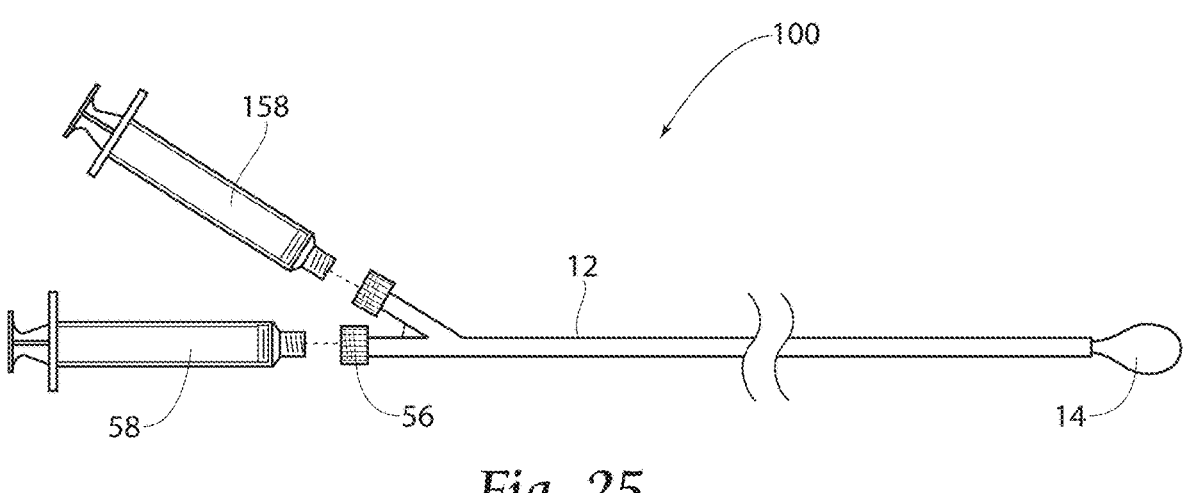
FIG. 25 depicts an assembly for the present invention wherein the assembly is capable of delivering liquids.

The present inventions and methods provide further improvements over the prior art, as is evident from FIG. 25. As noted previously in FIG. 19, it may be desirous to deliver a medicinal fluid to the treatment area. A system 100, along with a port 56 for attachment to the syringe 58 for expanding the inflatable member 14, could also include the attachment of an external fluid source, depicted in FIG. 25 as a 158 syringe. The system provides a simple arrangement for increasing volume in the inflatable member 14 and fluid to a treatment area. It will be appreciated and understood that the system 100 could be of any device to carry out the methods of the present invention and should not be considered to be limiting. Likewise, the external fluid source 58 should not be considered as requiring any specific arrangement. Provided a device would have a port that would allow fluid flow for the processes described herein, it would fall under the scope of the present invention.

Figure 25A:
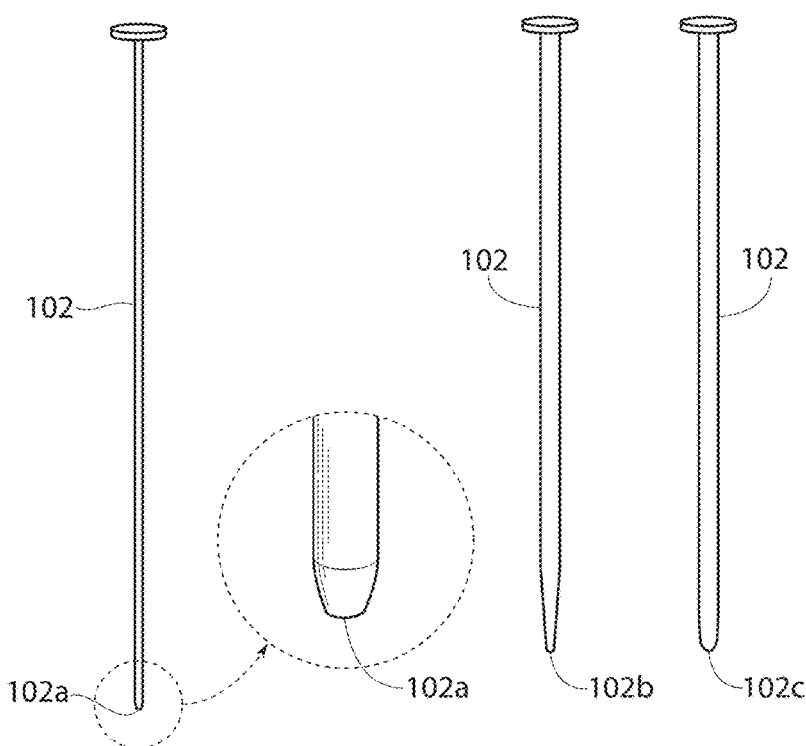
FIG. 25A depicts stylets used in the present invention with varying levels of sharpness for the tips of the cannulas.
Figure 26:
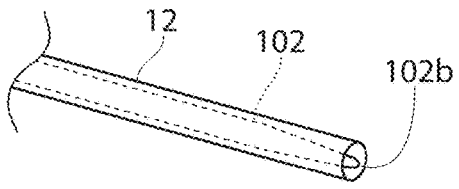
FIG. 26 demonstrates a partial perspective view of a stylet having a sharp tip for use with the present invention being housed within a cannula.

FIGS. 25A-32 provide even further improvements of the present invention. A plurality of styles or cannulated needles 102 are shown in FIG. 25A have varying degrees of sharpness on the tips, 102a-102c, for example Quincke Whitacre and Sprotte needles, commonly used. The stylets can also vary in dimensions, such as from 14 to 22 gauge French (diameter size), and various lengths (3-7 inch length).

As appreciated and understood with such procedures as described herein, there are different layers, e.g. skin and fascia (deep thick layer underneath the skin), that need to be navigated when performing such a procedure. Likewise, the present devices and procedures are used around sensitive nerves and the foramen. The devices and methods of the present invention are designed to be used in such differing areas of the body. For example, to penetrate the skin and the fascia, a sharp device may be desired to penetrate these layers, while a blunter device may be desirous when navigating around the nerves and the foramen. The delivery device and system 100 shown in FIG. 26 contemplates such considerations.

The delivery device 100 of FIG. 24 generally comprises the stylets 102 described in FIG. 25A, as well as the cannula 12 previously described. As shown, the cannula 12 houses the stylet having the generally sharp tip 102b.

Figure 27:
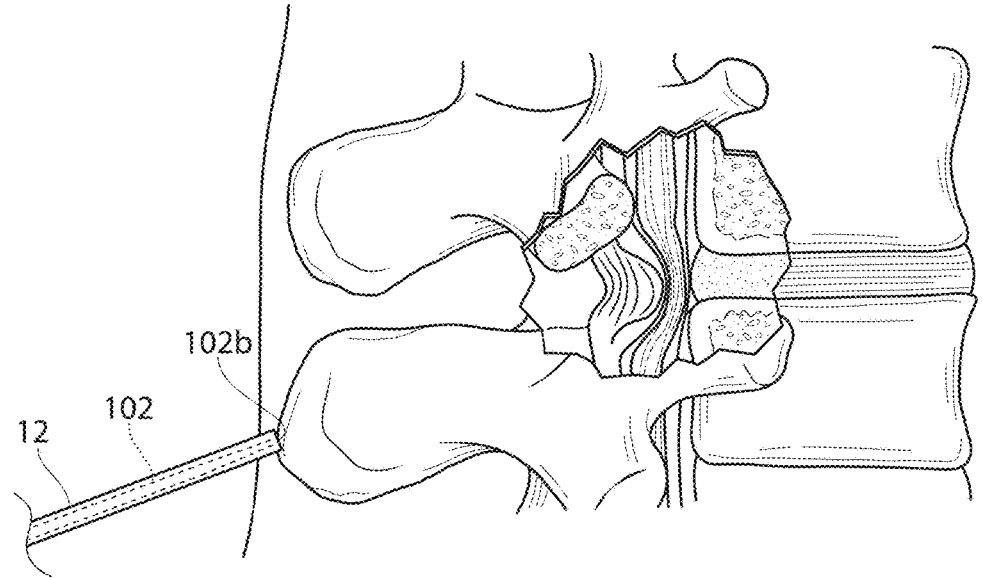
FIG. 27 shows the stylet of FIG. 26, with the cannula being inserted through the skin of the patient.
Figure 28:
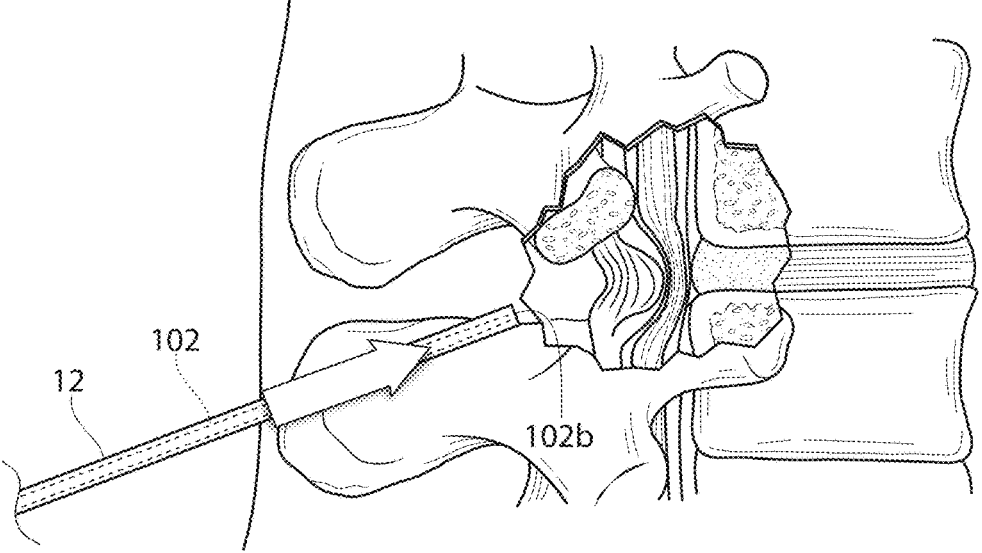
FIG. 28 depicts a further step in advancing the stylet and cannula shown in FIG. 27.
Figures 29, 30, 31:
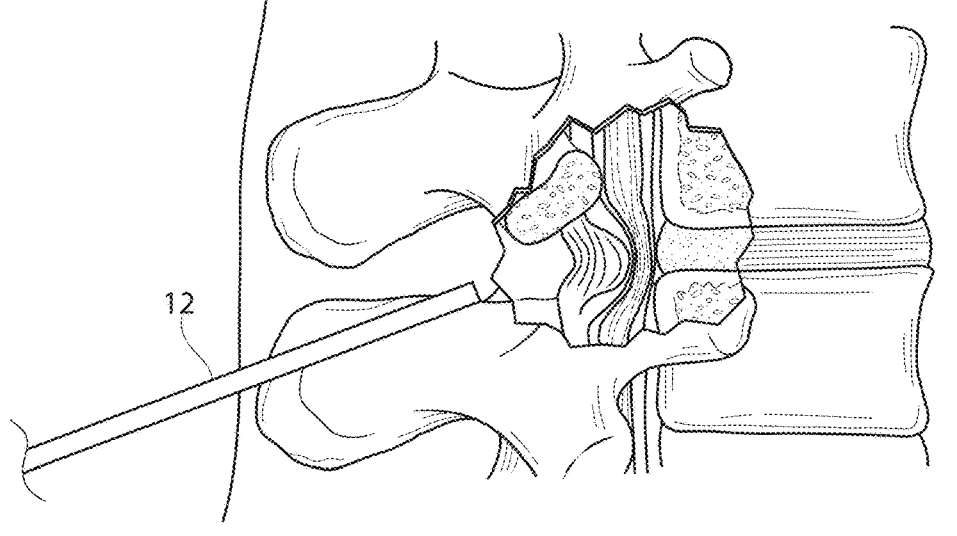
FIG. 29 depicts a further step, wherein the stylet is further advanced.
FIG. 30 demonstrates the cannula of FIG. 27 being replaced with a cannula having a blunt end.
FIG. 31 depicts a further step of the cannula of FIG. 30, wherein the blunt stylet is retracted through the cannula.

As shown in FIG. 27-29, the stylet 102 being used had the sharpened tip 102b, which allows easier insertion in passing through the skin and the fascia. The catheter is inserted until the cannula 12 and the stylet 102 approaches the treatment area (FIG. 28), and then retracted (FIG. 29).

Once a pathway is established, a stylet 102 having a blunt tip 102c will be inserted (FIG. 30) for continuing the procedure. The blunt tip 102c is preferable around the treatment area, so as not to cause any undue stress or trauma within the spinal cord area. The cannula 12 will then be used for delivering the inflatable member 14 (FIG. 32), as described in the previous Figures and processes. Preferably, the syringes 58 and 158 will be used to deliver volume and fluids, as necessary. It should be understood that the features described in the various procedures could be incorporated into any of the described processes and fall within the scope of the invention.

Figures 32, 33A, 33B, 33C:
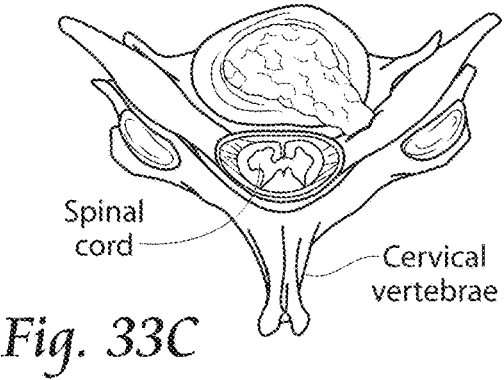
FIG. 32 depicts a step of the inflatable member being deployed into the treatment area.
FIGS. 33A-33C show a portion of the cervical vertebrae, with the vertebrae having issues associated with stenosis.

While the above processes have been discuss with respect to general vertebral stenosis, the present invention has also applications to the cervical vertebrae. As shown in FIGS. 33A-333C, thinning or compressed discs can lead to complications, including shoulder and arm pain (shown as shading in FIG. 35). The procedures previously used have

Figure 36:
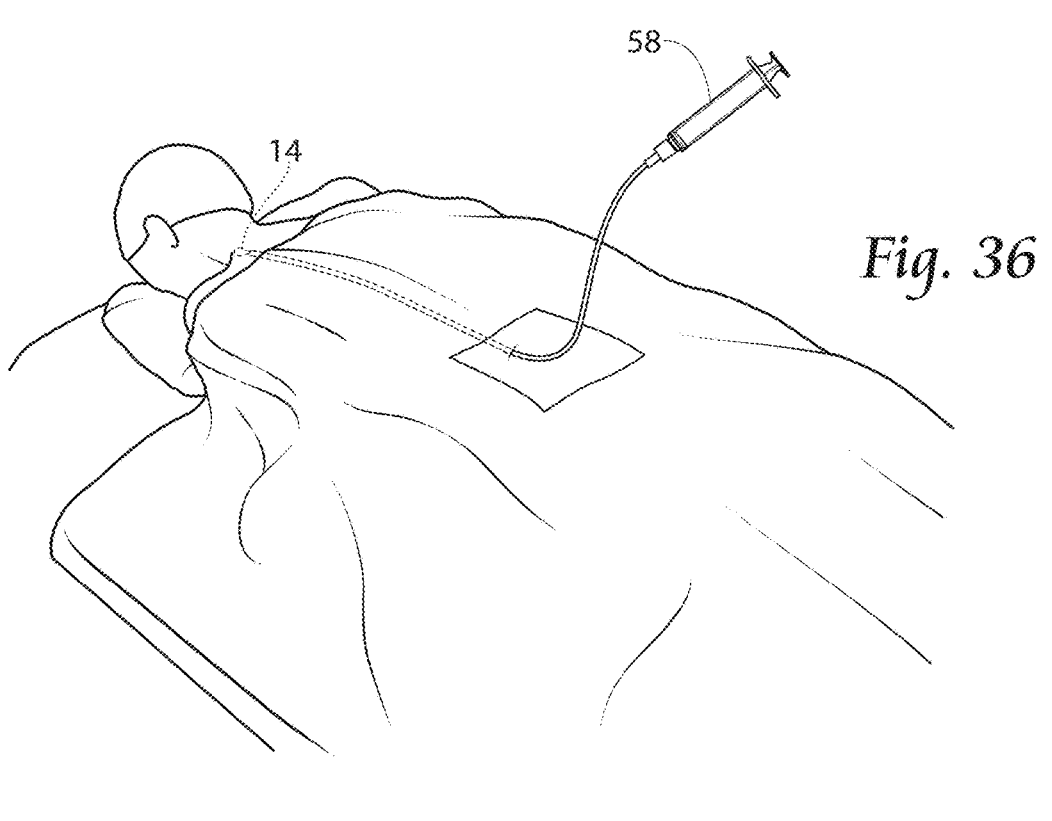
FIGS. 36 and 37 depict optional entry areas for the methods and assemblies of the present invention.
Figure 37:
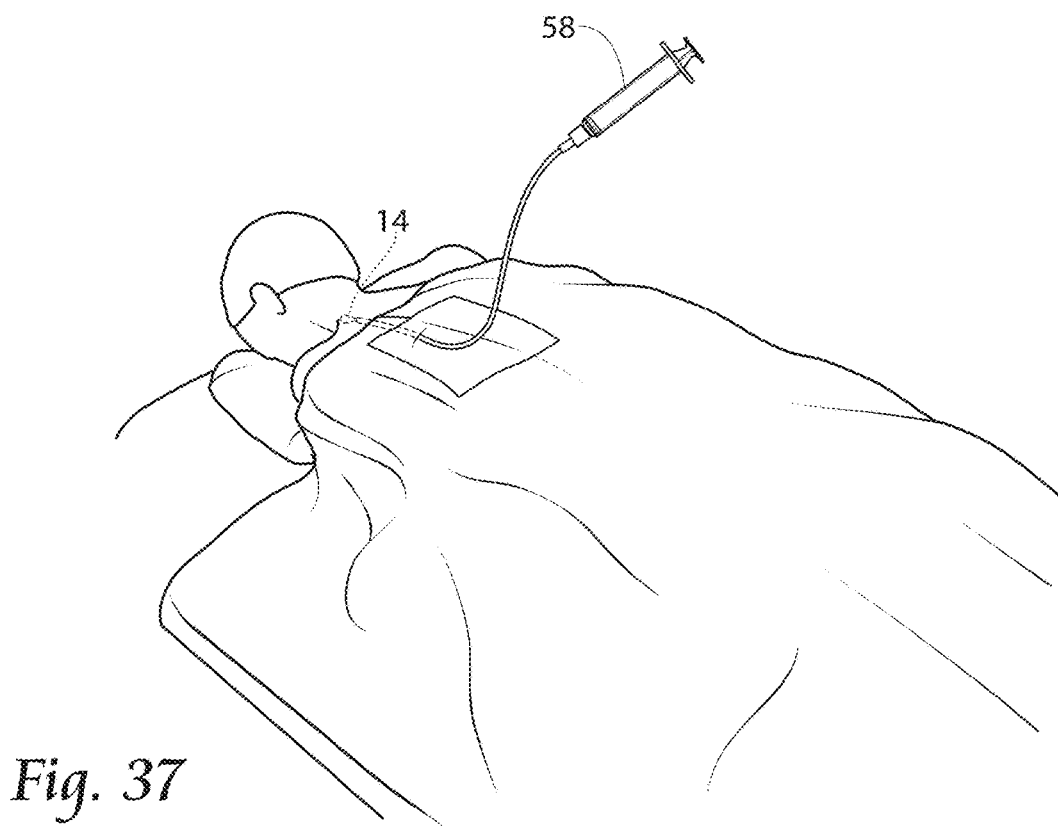

10 been contemplated and are capable of carrying out procedures to treat cervical stenosis. That is, the same delivery processes of delivering inflatable members As will be appreciated with all of these processes, whether treating any area of the spine, it is possible for the initial step for a laminotomy as being performed at various areas along the spine. For example FIG. 36 demonstrates an area closer associated with the lower back, for treating the thoracic or lumbar areas of the spine, while FIG. 37 is around the upper back area, easier to access treatment of cervical stenosis.

Figure 10:
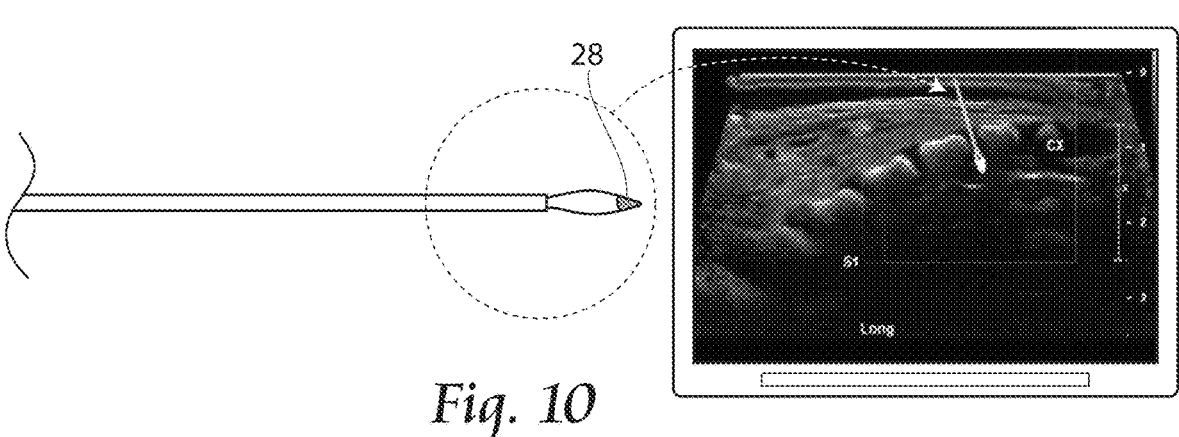
FIG. 10 is a partially cut-away view of the delivery system of the present invention, demonstrating an echogenic marker on the inflatable member in combination with an ultrasound imaging machine.
Figures 34, 35:
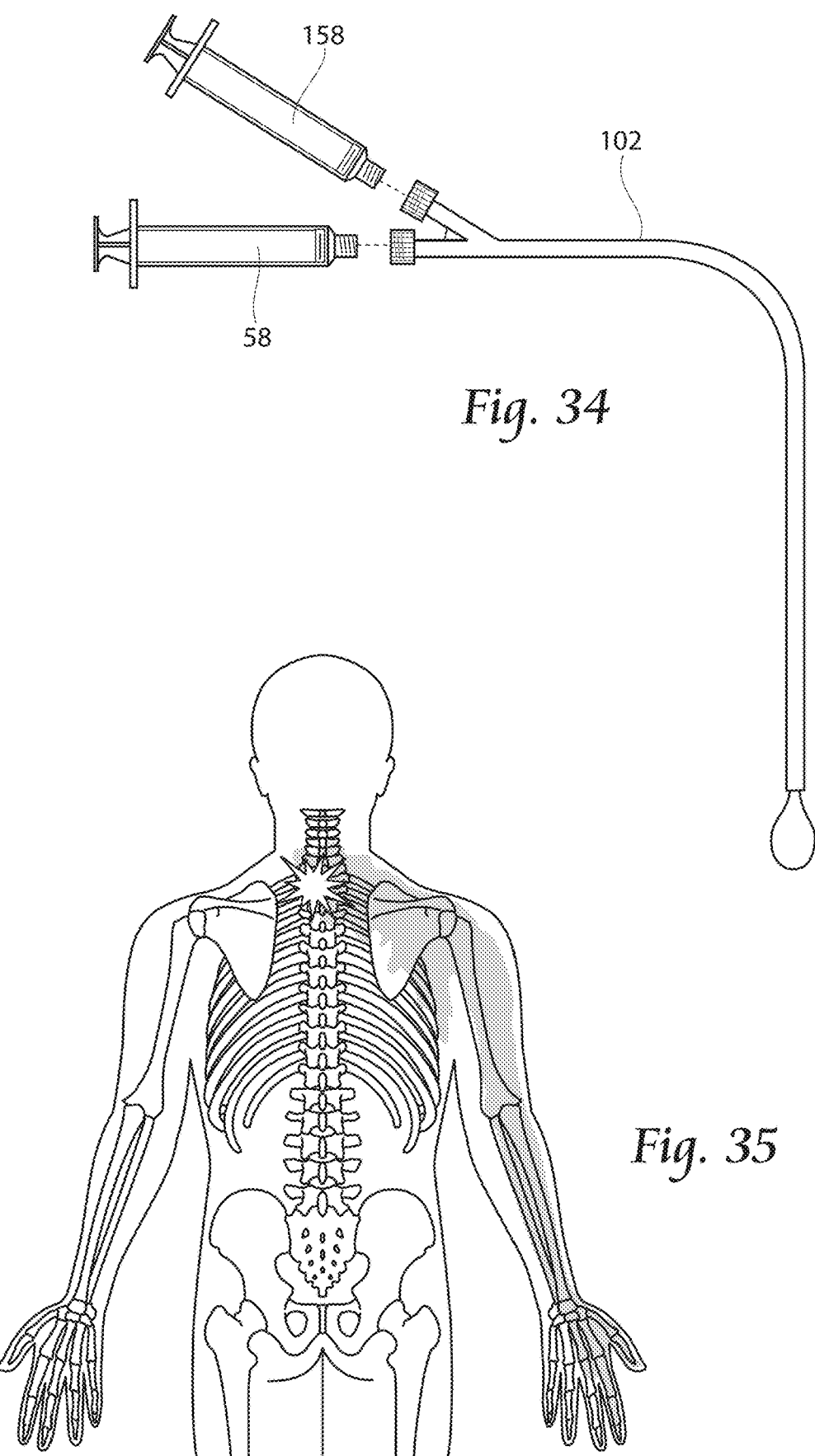
FIG. 34 shows an angled catheter used with the assembly of the present invention.
FIG. 35 demonstrates neck and arm pain that can be caused by the issues associated with the vertebrae depicted in FIGS. 33A-33C.

Because of the possibility of various entrance points, it is possible that the operator for the procedure is exposed to unnecessary X-ray exposure (see, e.g. FIG. 10). That is, because X-ray imaging is used during these processes, it is possible that, because of the various positions and angles, the operator of the cannula 12 may be unnecessarily exposed to radiation. For example, the use of contrast, e.g. dye, within the inflatable members 14 is common, so that the procedures can be used and tracked under X-ray imaging. The present invention minimizes this, by providing catheters having a bend or angle within them, as shown in FIG. 34. Thus, the operator may be able to insert the catheter at position that is not exposed to the X-ray radiation, while still being sufficiently close to the patient to carry out the procedures of the present invention.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed

The invention claimed is:

1. A system for treating impingement of a nerve of a spinal canal caused by spinal stenosis within a human body, said spinal canal including a vertebral foramen, the system comprising:
   a catheter;
   a plurality of inflatable members, said inflatable members being of varying sizes movable from a deflated to an inflated position, one of said inflatable member located within the catheter in a deflated position, said inflatable member capable of being advanced outwardly of said catheter, said inflatable member being sized and configure to alleviate the nerve impingement when in said inflated position; and
   a cannula for housing said catheter, said cannula having a blunt end with at least one removable stylet having a blunt end located internally of said cannula.

2. The system of claim 1 further comprising a second removable stylet having a sharp end for incision into the human body.

3. The system of claim 1 further comprising means for delivering fluid through the system to the treatment area.

4. The system of claim 3 wherein the delivering means comprises a syringe connectable to said cannula.

5. The system according to claim 1, wherein at least one of the inflatable members is spherical.

6. The system according to claim 1, wherein at least one of the inflatable members is dumbbell shaped.

7. The system according to claim 1 further comprising a marker for positioning said inflatable member.

8. The system according to claim 7, wherein the marker comprises radiopaque marker located on the inflatable member.

9. The systems according to claim 1, wherein the inflatable members are designed not to exceed a predetermined maximum volume.

\* \* \* \* \*